US012678238B2

(12) United States Patent
Diaz-Chiosa

(10) Patent No.: US 12,678,238 B2
(45) Date of Patent: Jul. 14, 2026

(54) REAL-TIME INSTRUMENT POSITION IDENTIFICATION AND TRACKING

(71) Applicant: Covidien LP, Mansfield, MA (US)

(72) Inventor: Olesea Diaz-Chiosa, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 534 days.

(21) Appl. No.: 18/108,043

(22) Filed: Feb. 10, 2023

(65) Prior Publication Data

US 2023/0363834 A1      Nov. 16, 2023

Related U.S. Application Data

(60) Provisional application No. 63/340,568, filed on May 11, 2022.

(51) Int. Cl.
| | |
|---|---|
| *A61B 34/00* | (2016.01) |
| *A61B 34/10* | (2016.01) |
| *A61B 34/20* | (2016.01) |
| *A61B 34/30* | (2016.01) |
| *A61B 34/37* | (2016.01) |

(52) U.S. Cl.
CPC .............. *A61B 34/25* (2016.02); *A61B 34/37* (2016.02); *A61B 2034/102* (2016.02); *A61B 2034/105* (2016.02); *A61B 2034/2072* (2016.02); *A61B 2034/301* (2016.02)

(58) Field of Classification Search
CPC .................. A61B 2034/2051; A61B 2090/373
See application file for complete search history.

(56) References Cited

U.S. PATENT DOCUMENTS

| | | | |
|---|---|---|---|
| 6,132,368 | A | 10/2000 | Cooper |
| 6,206,903 | B1 | 3/2001 | Ramans |
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |

(Continued)

OTHER PUBLICATIONS

Extended European Search Report issued in corresponding application EP 23172306.5 dated Sep. 15, 2023 (11 pages).

*Primary Examiner* — Angela M Hoffa
(74) *Attorney, Agent, or Firm* — Carter, DeLuca & Farrell, LLP

(57) ABSTRACT

A surgical robotic system includes a first robotic arm configured to hold a camera access port and an endoscopic camera inserted therethrough. The system also includes a plurality of secondary robotic arms each of which is configured to hold an instrument access port of a plurality of instrument access ports and a surgical instrument of a plurality of surgical instruments, each of which is configured to be inserted into one instrument access port of the plurality of instrument access ports. The system further includes a plurality of beacons. One beacon of the plurality of beacons is disposed on the camera access port and one beacon of the remaining plurality of beacons is disposed on one instrument access port of the plurality of instrument access ports. Each beacon of the plurality of beacons is configured to wirelessly communicate with each other. The system additionally includes a controller configured to determine a position of the endoscopic camera and the plurality of surgical instruments based on wireless communication between the beacons.

20 Claims, 10 Drawing Sheets

3-D Projection Dome

(56) References Cited

U.S. PATENT DOCUMENTS

| | | | |
|---|---|---|---|
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,468,265 B1 | 10/2002 | Evans et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,174,201 B2 * | 2/2007 | Govari | A61B 34/20 |
| | | | 600/424 |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,557,710 B2 * | 7/2009 | Sanchez | A61B 90/98 |
| | | | 340/286.07 |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,785 B2 | 11/2010 | Scully et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,374,723 B2 | 2/2013 | Zhao et al. | |
| 8,418,073 B2 | 4/2013 | Mohr et al. | |
| 8,419,717 B2 | 4/2013 | Diolaiti et al. | |
| 8,423,182 B2 | 4/2013 | Robinson et al. | |
| 8,452,447 B2 | 5/2013 | Nixon | |
| 8,454,585 B2 | 6/2013 | Whitman | |
| 8,499,992 B2 | 8/2013 | Whitman et al. | |
| 8,508,173 B2 | 8/2013 | Goldberg et al. | |
| 8,528,440 B2 | 9/2013 | Morley et al. | |
| 8,529,582 B2 | 9/2013 | Devengenzo et al. | |
| 8,540,748 B2 | 9/2013 | Murphy et al. | |
| 8,551,116 B2 | 10/2013 | Julian et al. | |
| 8,562,594 B2 | 10/2013 | Cooper et al. | |
| 8,594,841 B2 | 11/2013 | Zhao et al. | |
| 8,597,182 B2 | 12/2013 | Stein et al. | |
| 8,597,280 B2 | 12/2013 | Cooper et al. | |
| 8,600,551 B2 | 12/2013 | Itkowitz et al. | |
| 8,608,773 B2 | 12/2013 | Tierney et al. | |
| 8,620,473 B2 | 12/2013 | Diolaiti et al. | |
| 8,624,537 B2 | 1/2014 | Nowlin et al. | |
| 8,634,957 B2 | 1/2014 | Toth et al. | |
| 8,638,056 B2 | 1/2014 | Goldberg et al. | |
| 8,638,057 B2 | 1/2014 | Goldberg et al. | |
| 8,644,988 B2 | 2/2014 | Prisco et al. | |
| 8,666,544 B2 | 3/2014 | Moll et al. | |
| 8,668,638 B2 | 3/2014 | Donhowe et al. | |
| 8,746,252 B2 | 6/2014 | McGrogan et al. | |
| 8,749,189 B2 | 6/2014 | Nowlin et al. | |
| 8,749,190 B2 | 6/2014 | Nowlin et al. | |
| 8,758,352 B2 | 6/2014 | Cooper et al. | |
| 8,761,930 B2 | 6/2014 | Nixon | |
| 8,768,516 B2 | 7/2014 | Diolaiti et al. | |
| 8,786,241 B2 | 7/2014 | Nowlin et al. | |
| 8,790,243 B2 | 7/2014 | Cooper et al. | |
| 8,808,164 B2 | 8/2014 | Hoffman et al. | |
| 8,816,628 B2 | 8/2014 | Nowlin et al. | |

(56)         References Cited

U.S. PATENT DOCUMENTS

| | | | |
|---|---|---|---|
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,882,657 B2 | 11/2014 | Ohline et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 * | 8/2017 | Larkin ................. B25J 9/1694 |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,165 B2 | 10/2018 | Power |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,342,476 B2 * | 7/2019 | Schwartz ............ A61B 90/361 |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,893,899 B2 * | 1/2021 | Weber ................... A61B 18/14 |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |

(56)                References Cited

U.S. PATENT DOCUMENTS

| | | | |
|---|---|---|---|
| 10,952,801 B2 | 3/2021 | Miller et al. | |
| 10,965,933 B2 | 3/2021 | Jarc | |
| 10,966,742 B2 | 4/2021 | Rosa et al. | |
| 10,973,517 B2 | 4/2021 | Wixey | |
| 10,973,519 B2 | 4/2021 | Weir et al. | |
| 10,984,567 B2 | 4/2021 | Itkowitz et al. | |
| 10,993,773 B2 | 5/2021 | Cooper et al. | |
| 10,993,775 B2 | 5/2021 | Cooper et al. | |
| 11,000,331 B2 | 5/2021 | Krom et al. | |
| 11,013,567 B2 | 5/2021 | Wu et al. | |
| 11,020,138 B2 | 6/2021 | Ragosta | |
| 11,020,191 B2 | 6/2021 | Diolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 * | 11/2021 | Rabindran | B25J 9/06 |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 11,771,489 B2 * | 10/2023 | Weber | A61B 18/14 606/41 |
| 12,127,846 B2 * | 10/2024 | Schwartz | A61B 5/6811 |
| 12,357,400 B2 * | 7/2025 | Itkowitz | A61B 34/30 |
| 2003/0023161 A1 * | 1/2003 | Govari | A61B 5/06 600/423 |
| 2007/0268133 A1 * | 11/2007 | Sanchez | G08B 13/2462 340/568.1 |
| 2012/0053402 A1 | 3/2012 | Conlon et al. | |
| 2015/0038788 A1 | 2/2015 | Ohline et al. | |
| 2018/0014890 A1 | 1/2018 | Stanton et al. | |
| 2018/0297206 A1 * | 10/2018 | Larkin | A61B 34/10 |
| 2019/0192214 A1 * | 6/2019 | Weber | A61B 18/00 |
| 2020/0015923 A1 | 1/2020 | Scheib et al. | |
| 2020/0405401 A1 | 12/2020 | Shelton, IV et al. | |
| 2020/0405403 A1 | 12/2020 | Shelton, IV et al. | |
| 2021/0093372 A1 * | 4/2021 | Weber | A61B 18/00 |

* cited by examiner

82

No 3-D Dome
Please Insert
Instruments

23

81

80

Field of Vision
Overlay Over the
Scope Image

40

52

51

55a

AC

P

OR View of Primary
Beacon Established Upon
Endoscope Insertion

REAL-TIME INSTRUMENT POSITION IDENTIFICATION AND TRACKING

CROSS-REFERENCE TO RELATED APPLICATIONS

This application claims the benefit of and priority to U.S. Provisional Patent Application No. 63/340,568 filed May 11, 2022. The entire disclosure of the foregoing application is incorporated by referenced herein.

BACKGROUND

Surgical robotic systems may include a surgeon console controlling one or more surgical robotic arms, each including a surgical instrument having an end effector (e.g., forceps or grasping instrument). In operation, the robotic arm is moved to a position over a patient and the surgical instrument is guided into a small incision via a surgical access port or a natural orifice of a patient to position the end effector at a work site within the patient's body. The surgeon console includes hand controllers which translate user input into movement of the surgical instrument and/or end effector.

In robotic surgery, a surgeon may use multiple (e.g., up to four) instruments at a time, with one being a robotic endoscopic camera, two actively used instruments assigned to left- and right-hand controllers, and a reserve instrument. The general practice during endoscopic and robotic surgical procedures is to move the instruments in tandem with the camera to keep the instruments within a field of vision (FOV) of the camera. However, such tandem motion is not always possible, and the user needs to know real-time position of all instruments relative to the moving FOV. Thus, there is a need to provide real-time status of the instruments including those that are outside the FOV.

SUMMARY

The present disclosure provides a system and method for tracking instruments using sensors disposed on access ports to locate the instruments in real-time. A primary beacon may be disposed on an access port used by an endoscopic camera since the camera is the first instrument that is inserted into the patient. The beacon may be any suitable wireless transceiver configured to emit and receive wireless, e.g., radiofrequency, signals. The access port may have a mechanism that is engaged by insertion of the camera or an instrument into the access port. The mechanism may then activate the beacon. After insertion of the first access port, the patient is insufflated, and pneumoperitoneum is established. Thereafter, the remaining access ports are inserted along with corresponding instruments, thereby activating the beacons.

Beacons may be tracked by using any suitable tracking technique, such as triangulation or trilateration using distance and bearing information obtained from beacon transmissions. In particular, trilateration may be used to determine real-time distance of instrument beacons relative to FOV and triangulation may be used to calculate spatial angles and positions of instrument beacons.

The instruments and the endoscopic camera may be visualized as a graphical representation of the abdominal dome with the instrument position being projected in several views. The graphical representation may be displayed on any of the displays of the robotic system, e.g., control tower, surgeon console, etc. The graphical representation may be updated in real-time as the instrument(s) and the camera are moved. The positioning and angles may be communicated through port and arm connection through a wireless connection. Thus, as an instrument is withdrawn, the corresponding beacon is deactivated, and the graphical representation is updated to remove a virtual instrument. Audio and/or visual alerts may be issued by the robotic system when instruments outside the FOV are moving or touching specific anatomy. Furthermore, zones may be designated by the surgeon during the procedure using the graphical representation.

The disclosed tracking system makes the surgery safer for the patient and provides a 360-degree awareness inside the surgical site. The safety system also streamlines the surgery by allowing for troubleshooting of the intracorporeal instrument collisions. In addition, pre-operative imaging, e.g., CT scans, may be used along with graphical representations to enable for better visualization of the surgical site.

According to one embodiment of the present disclosure, a surgical robotic system is disclosed. The surgical robotic system includes a first robotic arm configured to hold a camera access port and an endoscopic camera inserted therethrough. The system also includes a plurality of secondary robotic arms each of which is configured to hold an instrument access port of a plurality of instrument access ports and a surgical instrument of a plurality of surgical instruments, each of which is configured to be inserted into one instrument access port of the plurality of instrument access ports. The system further includes a plurality of beacons. One beacon of the plurality of beacons is disposed on the camera access port and one beacon of the remaining plurality of beacons is disposed on one instrument access port of the plurality of instrument access ports. Each beacon of the plurality of beacons is configured to wirelessly communicate with each other. The system additionally includes a controller configured to determine a position of the endoscopic camera and the plurality of surgical instruments based on wireless communication between the beacons.

Implementations of the above embodiment may include one or more of the following features. According to one aspect of the above embodiment, the surgical robotic system may also include a display configured to show a graphical representation including the position of the endoscopic camera and the plurality of surgical instruments. The graphical representation may include a three-dimensional model of a surgical site and models of the endoscopic camera and the plurality of surgical instruments. The display may be further configured to show a cone representing a field of view of the endoscopic camera. The graphical representation may include a two-dimensional map of a surgical site and symbols representing the endoscopic camera and the plurality of surgical instruments. The display may be further configured to show a circle representing a field of view of the endoscopic camera. The display may be also configured to display a video feed of a field of view of the endoscopic camera and a representation of at least one of direction or distance of a surgical instrument of the plurality of surgical instruments located outside the field of view.

According to another embodiment of the present disclosure, a surgical robotic system is disclosed. The surgical robotic system includes a plurality of access ports and a plurality of surgical devices, each of which is configured to be inserted into one access port of the plurality of access ports. The system also includes a plurality of beacons, each of which is disposed on one access port of the plurality of access ports. Each beacon of the plurality of beacons is configured to wirelessly communicate with each other. The system further includes a controller configured to determine a position of each surgical device of the plurality of surgical devices based on wireless communication between the beacons.

Implementations of the above embodiment may include one or more of the following features. According to one aspect of the above embodiment, the surgical robotic system may include a display configured to show a graphical representation having the position of each surgical device. The graphical representation may include a three-dimensional model of a surgical site and models of the plurality of surgical devices. The graphical representation may also include a two-dimensional map of a surgical site and symbols representing of the plurality of surgical devices. The plurality of surgical devices may include at least one endoscopic camera. The plurality of surgical devices may include a plurality of surgical instruments. Each beacon of the plurality of beacons is configured to obtain at least one parameter of the wireless communication. The parameter of the wireless communication may include at least one of time of flight or angle of arrival measurements. The controller may be further configured to determine the position of each surgical device of the plurality of surgical devices using at least one trilateration or triangulation based on the parameter of the wireless communication.

According to a further embodiment of the present disclosure, a method for tacking position of surgical robotic instruments is disclosed. The method may include activating a plurality of beacons, each of which is disposed on one access port of a plurality of access ports. Each beacon of the plurality of beacons is configured to wirelessly communicate with each other. The method also includes determining a position of each surgical device of a plurality of surgical devices each of which is inserted into one access port of the plurality of access ports based on wireless communication between the beacons. The method further includes displaying a graphical representation having the position of each surgical device.

Implementations of the above embodiment may include one or more of the following features. According to one aspect of the above embodiment, the method further includes displaying at least one of a three-dimensional model of a surgical site and models of the plurality of surgical devices or a two-dimensional map of a surgical site and symbols representing of the plurality of surgical devices. The parameter of the wireless communication may include at least one of time of flight or angle of arrival measurements. The method may further include determining the position of each surgical device of the plurality of surgical devices using at least one trilateration or triangulation based on the parameter of the wireless communication.

BRIEF DESCRIPTION OF THE DRAWINGS

Various embodiments of the present disclosure are described herein with reference to the drawings wherein.

DETAILED DESCRIPTION

Figure 1:
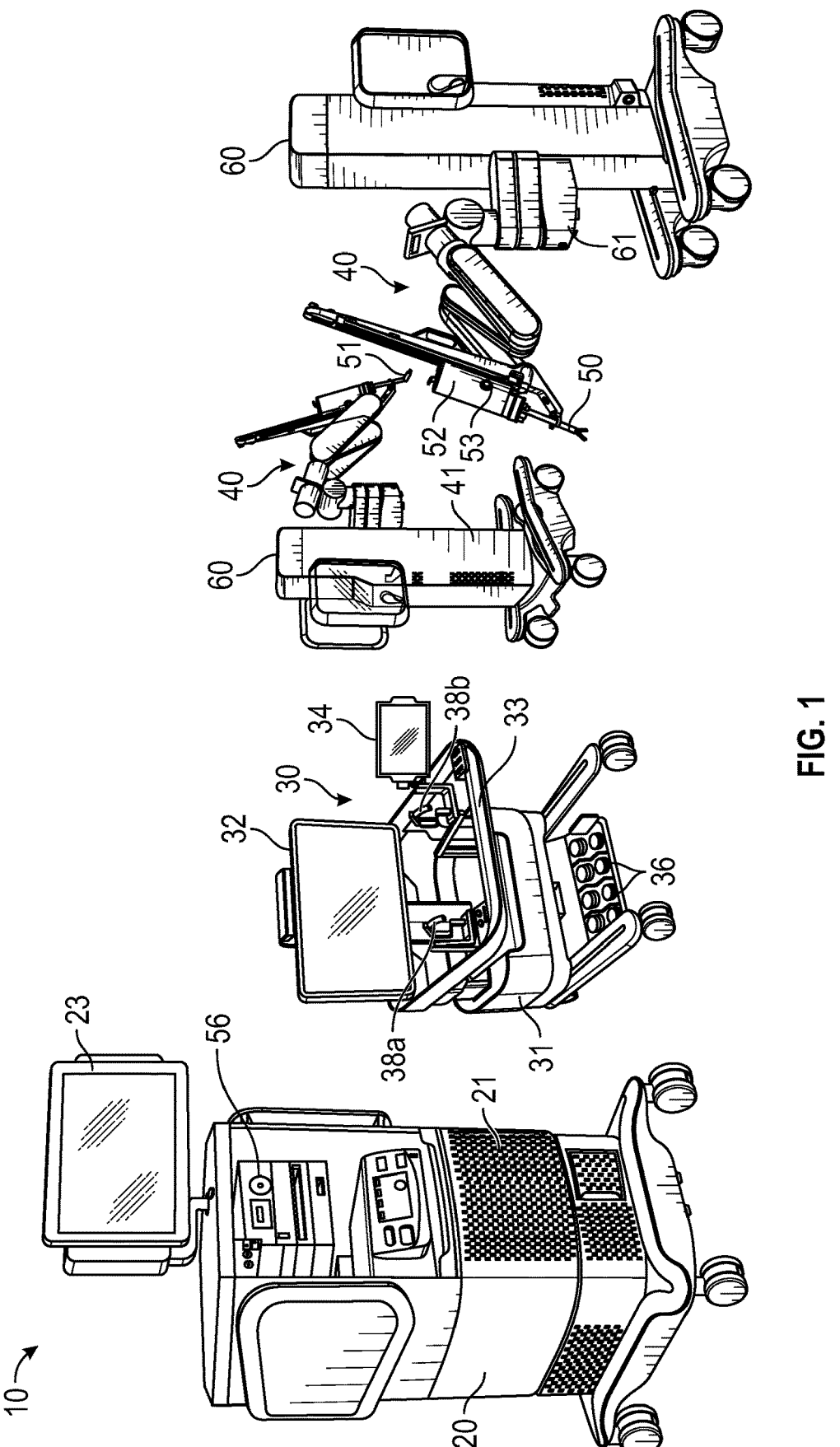
FIG. 1 is a perspective view of a surgical robotic system including a control tower, a console, and one or more surgical robotic arms each disposed on a mobile cart according to an embodiment of the present disclosure.

Embodiments of the presently disclosed surgical robotic system are described in detail with reference to the drawings, in which like reference numerals designate identical or corresponding elements in each of the several views. As used herein the term "proximal" refers to the portion of the surgical robotic system and/or the surgical instrument coupled thereto that is closer to a base of a robot, while the term "distal" refers to the portion that is farther from the base of the robot.

As will be described in detail below, the present disclosure is directed to a surgical robotic system, which includes a surgeon console, a control tower, and one or more mobile carts having a surgical robotic arm coupled to a setup arm. The surgeon console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgeon console 30 and one or more movable carts 60. Each of the movable carts 60 includes a robotic arm 40 having a surgical instrument 50 removably coupled thereto. The robotic arms 40 also couple to the movable cart 60. The robotic system 10 may include any number of movable carts 60 and/or robotic arms 40.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include the endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 and output the processed video stream.

The surgeon console 30 includes a first display 32, which displays a video feed of the surgical site provided by camera 51 of the surgical instrument 50 disposed on the robotic arm 40, and a second display 34, which displays a user interface for controlling the surgical robotic system 10. The first and second displays 32 and 34 are touchscreens allowing for displaying various graphical user inputs.

The surgeon console 30 also includes a plurality of user interface devices, such as foot pedals 36 and a pair of handle controllers 38a and 38b which are used by a user to remotely control robotic arms 40. The surgeon console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the handle controllers 38a and 38b.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-1203 standard for wireless personal area networks (WPANs)).

The computers 21, 31, 41 may include any suitable processor (not shown) operably connected to a memory (not shown), which may include one or more of volatile, nonvolatile, magnetic, optical, or electrical media, such as read-only memory (ROM), random access memory (RAM), electrically-erasable programmable ROM (EEPROM), nonvolatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
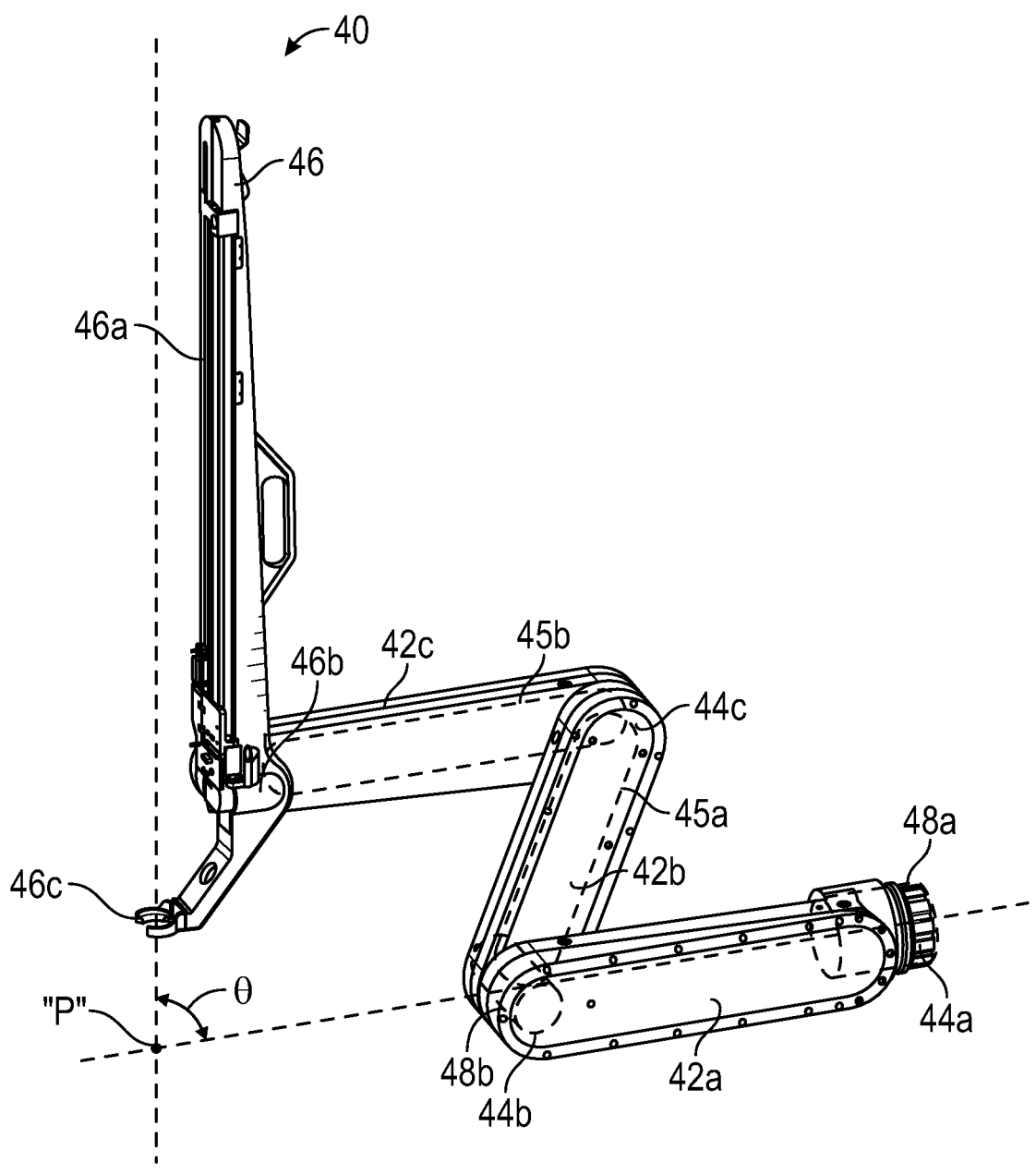
FIG. 2 is a perspective view of a surgical robotic arm of the surgical robotic system of FIG. 1 according to an embodiment of the present disclosure.
Figure 3:
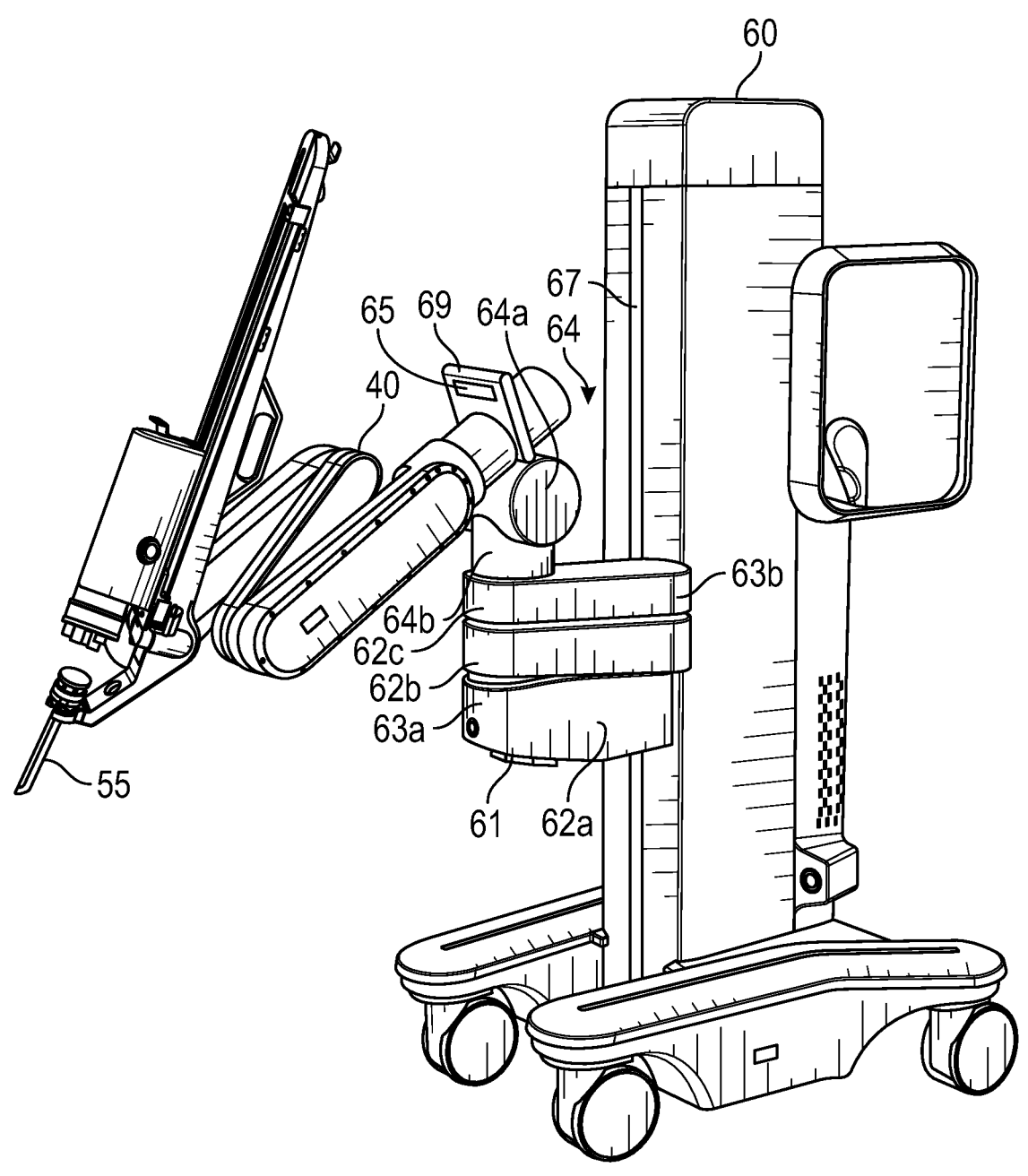
FIG. 3 is a perspective view of a mobile cart having a setup arm with the surgical robotic arm of the surgical robotic system of FIG. 1 according to an embodiment of the present disclosure.

With reference to FIG. 2, each of the robotic arms 40 may include a plurality of links 42a, 42b, 42c, which are interconnected at joints 44a, 44b, 44c, respectively. Other configurations of links and joints may be utilized as known by those skilled in the art. The joint 44a is configured to secure the robotic arm 40 to the mobile cart 60 and defines a first longitudinal axis. With reference to FIG. 3, the mobile cart 60 includes a lift 67 and a setup arm 61, which provides a base for mounting of the robotic arm 40. The lift 67 allows for vertical movement of the setup arm 61. The mobile cart 60 also includes a display 69 for displaying information pertaining to the robotic arm 40. In embodiments, the robotic arm 40 may include any type and/or number of joints.

The setup arm 61 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 includes controls 65 for adjusting movement of the links 62a, 62b, 62c as well as the lift 67. In embodiments, the setup arm 61 may include any type and/or number of joints.

The third link 62c may include a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The actuator 48b of the joint 44b is coupled to the joint 44c via the belt 45a, and the joint 44c is in turn coupled to the joint 46b via the belt 45b. Joint 44c may include a transfer case coupling the belts 45a and 45b, such that the actuator 48b is configured to rotate each of the links 42b, 42c and a holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. In other words, the pivot point "P" is a remote center of motion (RCM) for the robotic arm 40. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

With reference to FIG. 2, the holder 46 defines a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c. During endoscopic procedures, the instrument 50 may be inserted through an endoscopic access port 55 (FIG. 3) held by the holder 46. The holder 46 also includes a port latch 46c for securing the access port 55 to the holder 46 (FIG. 2).

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
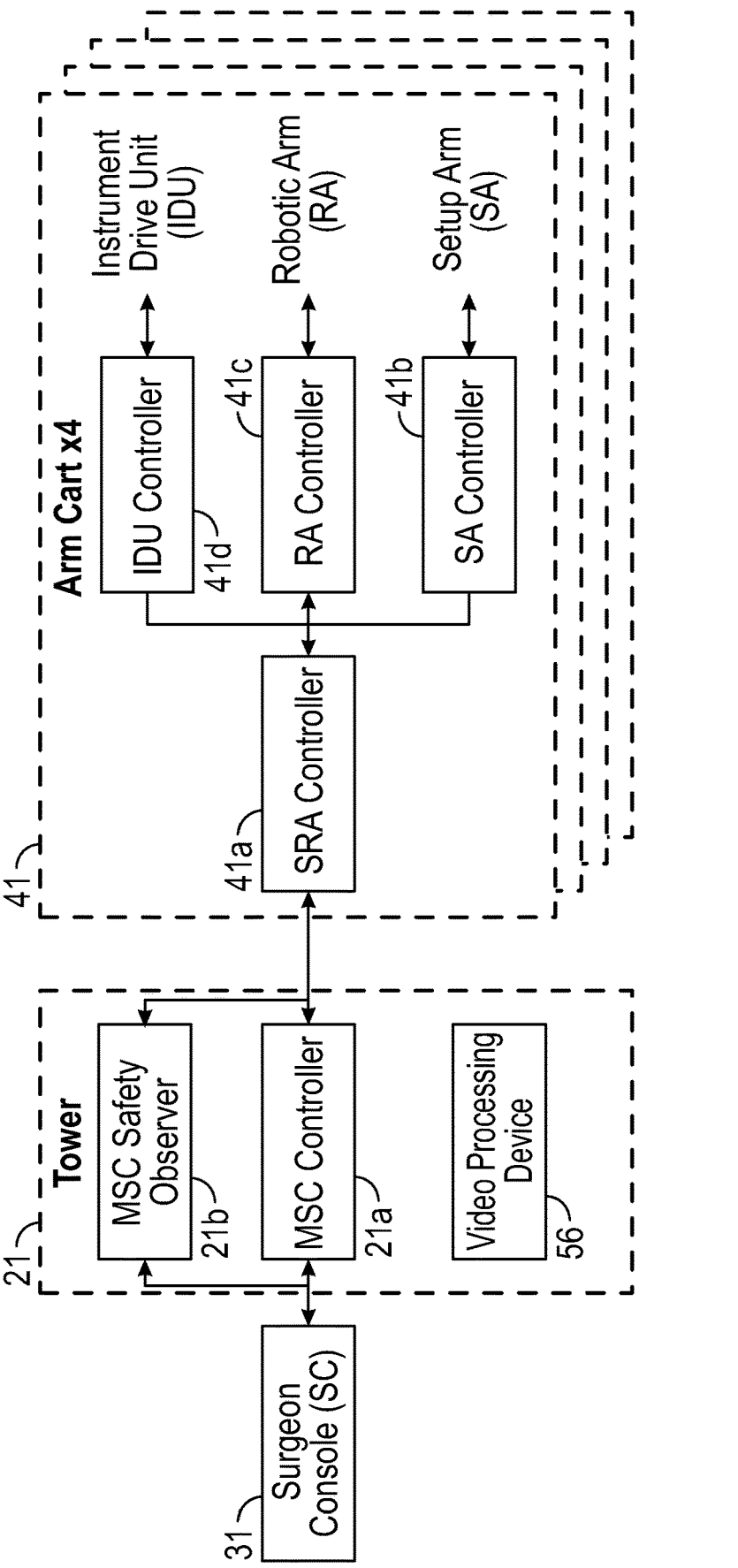
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgeon console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives the actual joint angles measured by encoders of the actuators 48a and 48b and uses this information to determine force feedback commands that are transmitted back to the computer 31 of the surgeon console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the mobile cart 60, the robotic arm 40, and the IDU 52. The main cart controller 41a also communicates actual joint angles back to the controller 21a.

Each of joints 63a and 63b and the rotatable base 64 of the setup arm 61 are passive joints (i.e., no actuators are present therein) allowing for manual adjustment thereof by a user. The joints 63a and 63b and the rotatable base 64 include brakes that are disengaged by the user to configure the setup arm 61. The setup arm controller 41b monitors slippage of each of joints 63a and 63b and the rotatable base 64 of the setup arm 61, when brakes are engaged or can be freely moved by the operator when brakes are disengaged, but do not impact controls of other joints. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled in response to a pose of the handle controller controlling the robotic arm 40, e.g., the handle controller 38a, which is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controllers 38a may be embodied as a coordinate position and roll-pitch-yaw (RPY) orientation relative to a coordinate reference frame, which is fixed to the surgeon console 30. The desired pose of the instrument 50 is relative to a fixed frame on the robotic arm 40. The pose of the handle controller 38a is then scaled by a scaling function executed by the controller 21a. In embodiments, the coordinate position may be scaled down and the orientation may be scaled up by the scaling function. In addition, the controller 21a may also execute a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

Figure 5:
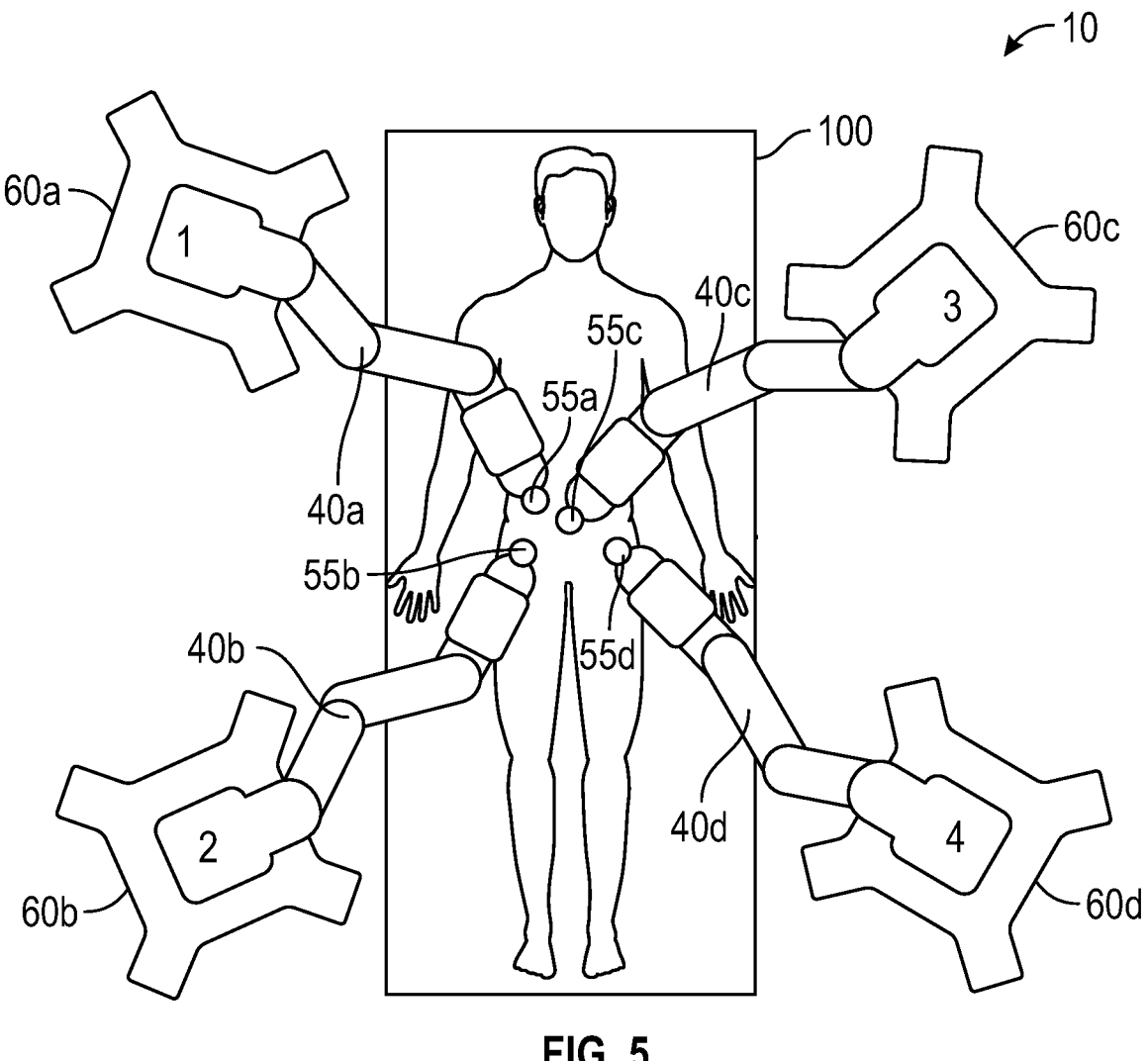
FIG. 5 is a plan schematic view of movable carts of FIG. 1 positioned about a surgical table according to an embodiment of the present disclosure.

With reference to FIG. 5, the surgical robotic system 10 is setup around a surgical table 100. The system 10 includes a plurality of movable carts 60a-d, which may be numbered "1" through "4." During setup, each of the carts 60a-d are positioned around the surgical table 100. Position and orientation of the carts 60a-d depends on a plurality of factors, such as placement of a plurality of ports 55a-d, which in turn, depends on the surgery being performed. Once the port placement is determined, the ports 55a-d are inserted into the patient, each of the robotic arms 40a-d are aligned to achieve a desired configuration of each of their respective joints, and carts 60a-d are positioned to insert instruments 50 and the endoscopic camera 51 into corresponding ports 55a-d.

Figure 6:
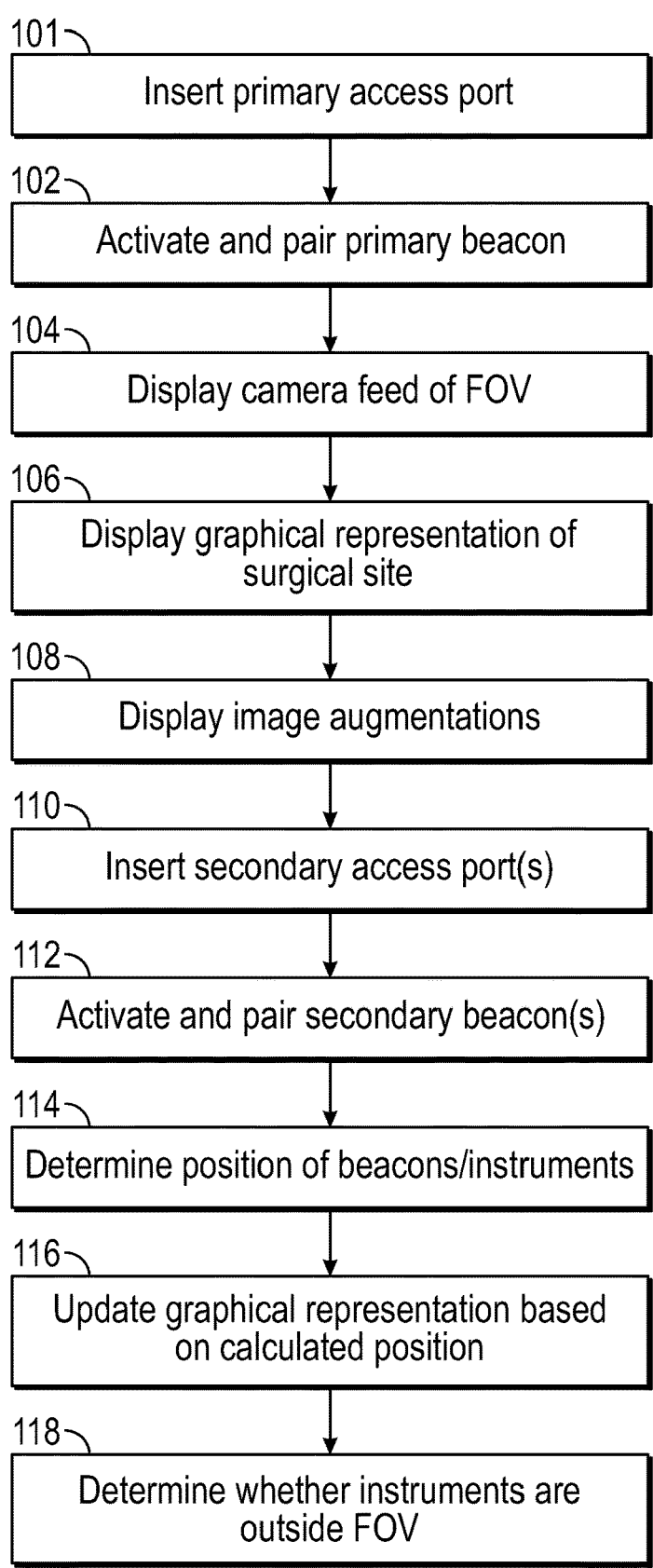
FIG. 6 is a flow chart of a method of using an instrument positional tracking according to an embodiment of the present disclosure.
Figure 7:
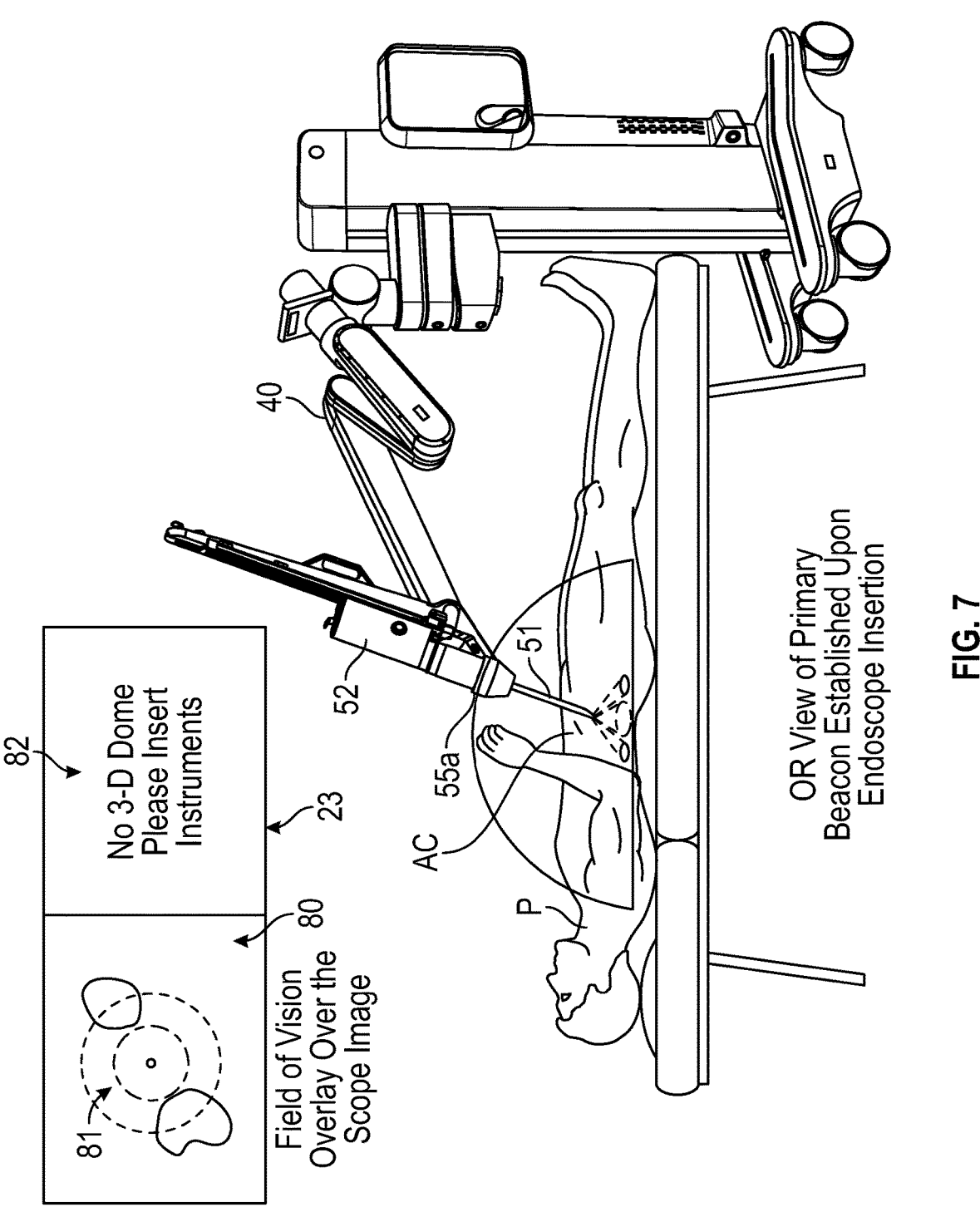
FIG. 7 is a schematic diagram of an endoscopic camera inserted into a patient and a display showing a first display region and a second display region according to an embodiment of the present disclosure.

With reference to FIGS. 6 and 7, a primary access port 55a is inserted into a patient "P" at step 101. The primary access port 55a is used insufflate the abdominal cavity "A" and to establish pneumoperitoneum. The access port 55a also includes a beacon 70 disposed on a cannula 57. The beacon 70 may include a transceiver and a receiver configured to communicate via any suitable wireless communication protocol (e.g., Bluetooth, WiFi, 5G, etc.)

Figures 8, 9:
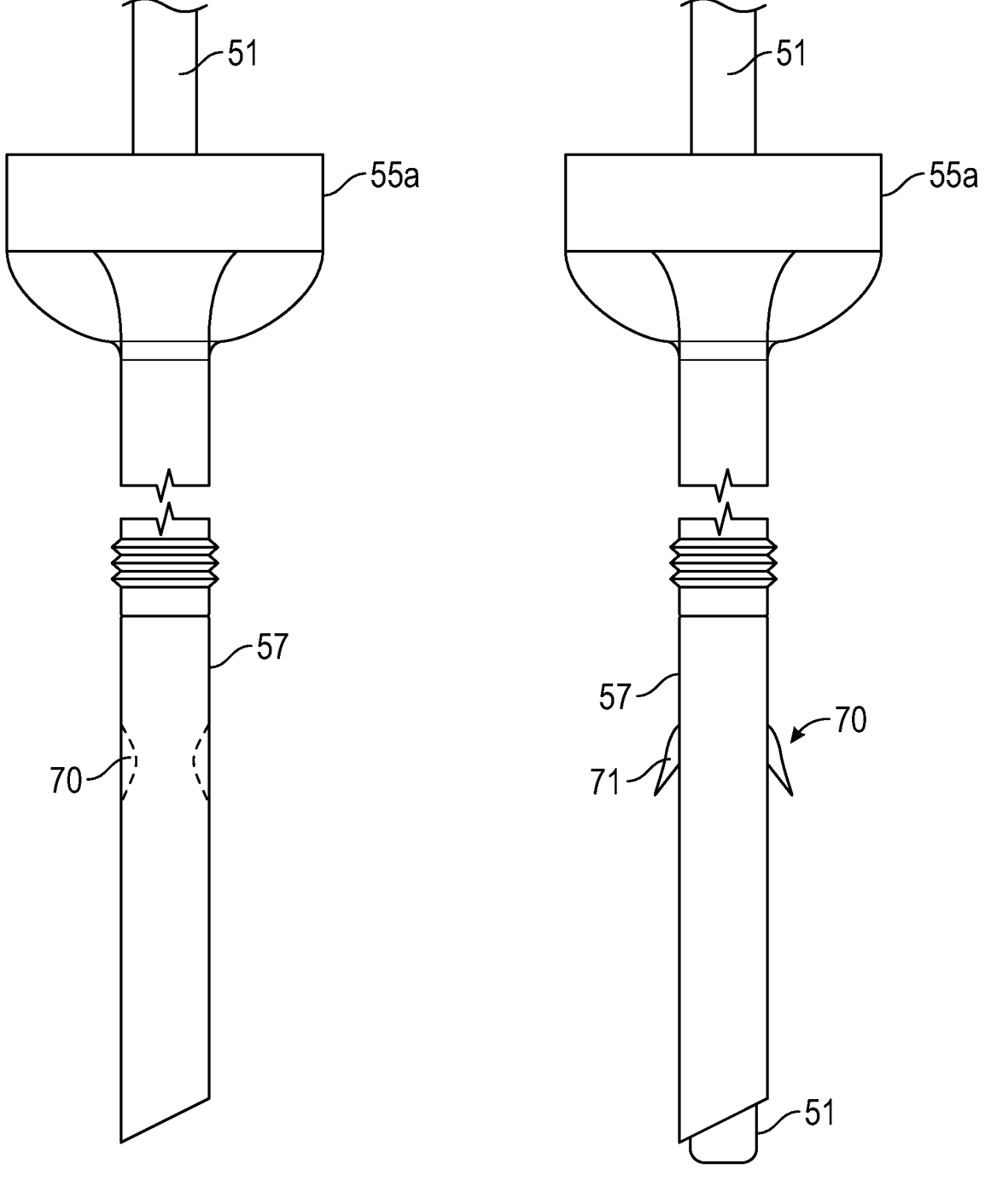
FIG. 8 is a side view of an access port in an inactive configuration according to an embodiment of the present disclosure.
FIG. 9 is a side view of the access port in an active configuration according to an embodiment of the present disclosure.

The beacon 70 is activated and paired at step 102. The beacon 70 may include one or more deployable wings 71 which are folded when the beacon 70 is in a deactivated state as shown in FIG. 8 and fold out when the beacon 70 is an activated state as shown in FIG. 9. The wings 71 are optional and activation status may be indicated in any suitable manner including but not limited to, LED disposed on the cannula 57 or a hub of the access port 55a. In embodiments, the indicator of the activation status may be indicated via a GUI displayed on any of the displays 23, 32, 34.

The beacon 70 may be activated upon insertion of the endoscopic camera 51 into the access port 55a. Activation may be done in response by a mechanical or electrical engagement by insertion of the endoscopic camera 51 through the access port 55, e.g., contacting a limit switch, capacitive switch, or any other contact or proximity detection device. In further embodiments, the beacon 70 may be activated by the controller 21a in response to detecting insertion of the endoscopic camera 51, e.g., based on travel of the IDU 52 along the sliding mechanism 46a.

During or after activation, the beacon 70 is also paired with the controller 21a via a wireless transceiver (not shown) configured to wirelessly communicate with the beacon 70. The controller 21a receives wireless data from the beacon 70, including distance and direction information of the beacon 70 based on time of flight, angle of arrival, and other wireless signal parameters.

Figure 10:
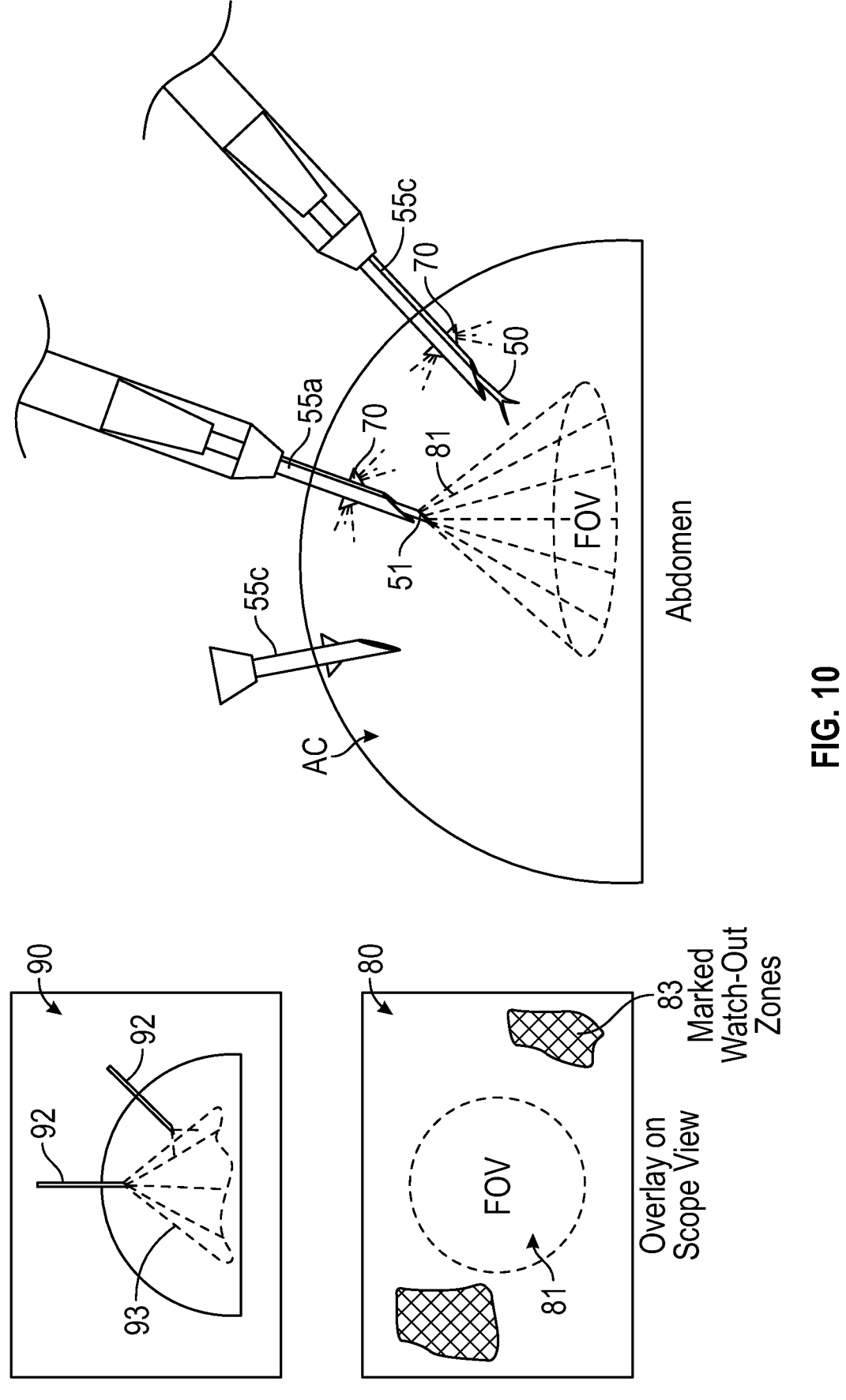
FIG. 10 is a side schematic view of the endoscopic camera, a first access port and a second access port in an active configuration, and a third access port in an inactive configuration and the display showing graphical representations according to an embodiment of the present disclosure.

With reference to FIGS. 6 and 10, at step 104, a camera feed 80 of the endoscopic camera 51 is shown in the first display 32. The camera feed 80 includes a field of view (FOV) 81 as shown in FIG. 7. The system 10 also displays user instructions 82 to setup tracking and other messages. The camera feed 80 and user instructions 82 may be displayed in any suitable manner, e.g., as overlays, different regions, and/or on any of the other displays of the system 10, e.g., display 23 of the control tower 20 and/or the second display 34.

In addition, at step 106 a graphical representation 90 of a surgical site is shown along with the camera feed 80 as shown in FIG. 10. The graphical representation 90 displays a three-dimensional (3D) (i.e., computer generated) model "M" of a surgical site, e.g., the abdominal cavity "AC", along with models 92 the endoscopic camera 51 and instruments 50 that are inserted into the abdominal cavity "A." The graphical representation 90 may be generated by the controller 21a from a plurality of 3D models, which may be stored in a library and may be loaded based on the model or any other identifier of the surgical devices (i.e., endoscopic camera 51 and instruments 50). The 3D model of the abdominal cavity "A" may be generated using machine learning image processing algorithms, e.g., using depth mapping techniques and textures extracted from the camera feed 80. The graphical representation 90 may also have an adjustable viewpoint, which allows the user to move, pan, zoom, tilt, rotate, etc. In embodiments, the viewpoint may be adjusted automatically by the controller 21a based on the task being performed by the system 10, e.g., zoom in on an instrument being used, tissue being manipulated, etc.

Once the camera feed 80 is established, the system 10 is also configured to implement various surgeon aids and artificial intelligence augmentations at step 108. In embodiments, critical structures may be manually or automatically (i.e., using machine learning image processing techniques) identified and marked by the controller 21a as critical zones 83 to prevent operation of the instruments 50 on the critical structures. In addition, other areas may be demarcated by a user as critical zones 83 by drawing a virtual wall around any area at the surgical site. A virtual wall prevents the system 10 from processing any user inputs that would result in movement or operation of the instruments 50 in those areas.

Figure 11:
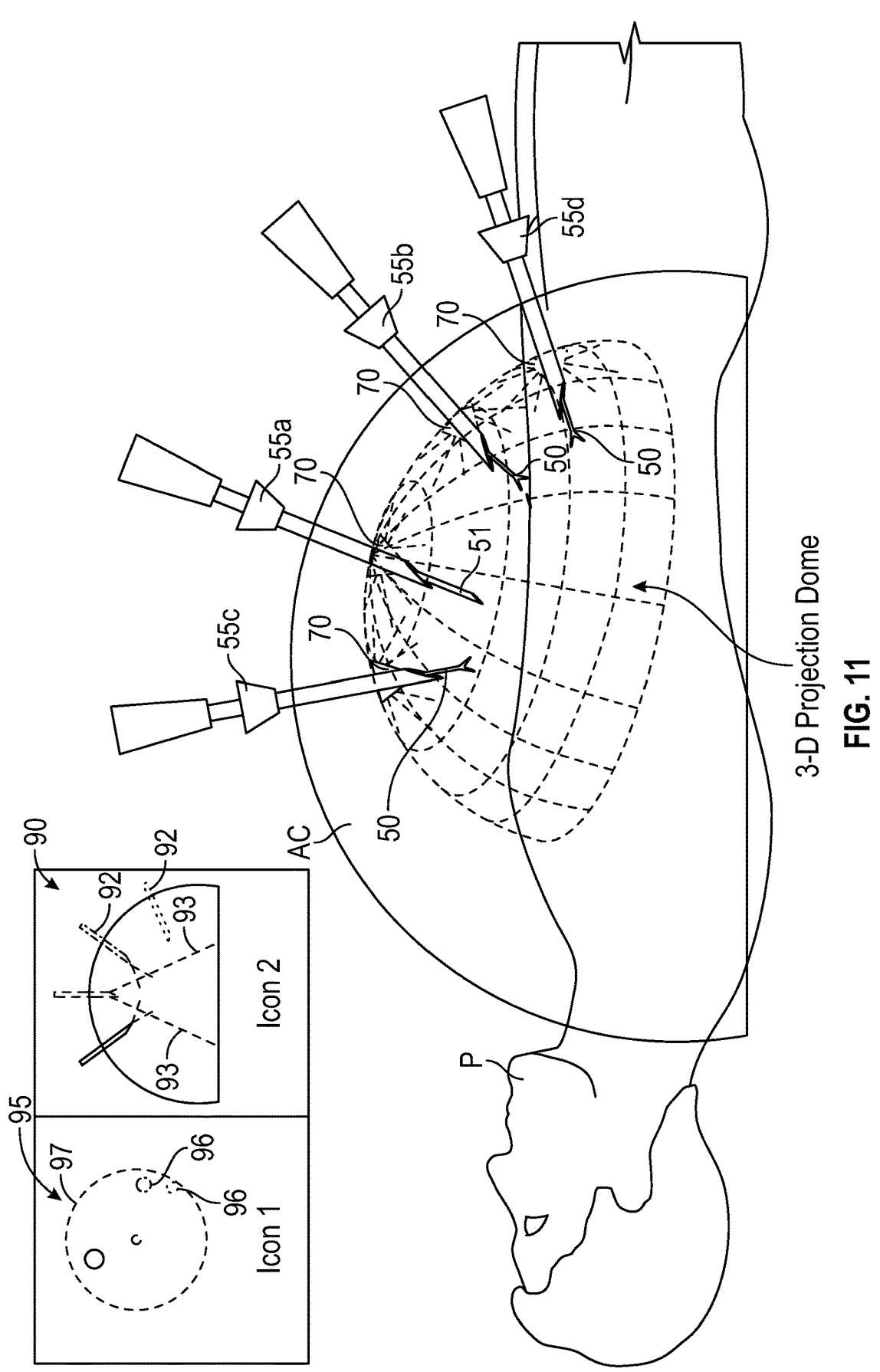
FIG. 11 is a side schematic view of the endoscopic camera and three access ports in an active configuration inserted into the patient and the display showing the graphical representations according to an embodiment of the present disclosure.

After the first beacon 70 is paired, the rest of the access ports 55b-d (e.g., one or more) are inserted into the abdominal cavity "A" as shown in FIG. 11. At step 110, one or more of the access ports 55b-d are inserted in the same manner as described above with respect to the primary access port 55a. Each of the secondary access ports 55b-d includes a beacon 70. At step 112, each of the instruments 50 is inserted into the secondary access port 55b-d and corresponding beacons 70 are activated and paired in the same manner as described above.

At step 114, once all of the instruments 50 are inserted and corresponding beacons 70 are activated, position of the beacons 70 is determined. In particular, the beacons 70 are used to determine position of the endoscopic camera 51 and the instruments 50 in 3D space. Three or more beacons 70 may be used to determine position of the beacons 70 using trilateration or triangulation based on time-of-flight and angle-of-arrival data from each of the beacons 70. In particular, each of the beacons 70 continuously communicate with each other. Triangulation may be used by the controller 21a in situations where bearing of each of the beacons 70, i.e., angles therebetween, are known. Trilateration may be used when distances between each of the beacons 70 are known.

The beacons 70 are configured to measure time-of-flight of interrogation signals, which is used to determine the distance between the beacons 70. Each of the beacons 70 also measures angle-of-arrival of interrogation signals, which is used to determine the angles between the beacons 70. The distance and angles between the beacons 70 may be used by the controller 21a to determine relative position of the beacons 70, which is equivalent to the position of the endoscopic camera 51 and the instruments 50.

At step 116, the camera feed 80 and the graphical representation 90 are updated in real-time based on the position of the beacons 70. With reference to FIG. 11, the graphical representation 90 moves the models 92 in response to movement of the beacons 70, which corresponds to movement of the endoscopic camera 51 and the instruments 50. In embodiments, a second graphical representation 95 may be displayed along with the graphical representation 90. The second graphical representation 95 may represent a top-down map of the abdominal cavity "AC" with various symbols 96, and/or descriptors representing the position of the endoscopic camera 51 and the instruments 50.

In embodiments, the FOV 81 may be represented as a cone 93 in the graphical representation 90 or as a circle 97 allowing for the user to see the location of the endoscopic camera 51 and the instruments 50 even when they are outside the FOV 81. At step 118, the controller 21a is also configured to automatically determine when the instruments 50 are outside the FOV 81. Image processing algorithms may be used to analyze the FOV 81 to detect instruments 50 that are present therein. In addition, presence of the instruments 50 may be determined based on the graphical representations 90 and 95 and/or the calculations performed by the controller 21a used to generate the graphical representations 90 and 95. Thus, the controller 21a may determine if the models 92 or the symbols 96 are located outside the cone 93 or the circle 97, and if so, the controller 21a may output an alert or a representation of direction and distance on the camera feed 80 as an overlay.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
a camera access port and a plurality of instrument access ports;
a first robotic arm configured to hold the camera access port and an endoscopic camera inserted therethrough;
a plurality of secondary robotic arms each of which is configured to hold one instrument access port of the plurality of instrument access ports and a surgical instrument of a plurality of surgical instruments, wherein each of the plurality of surgical instruments is configured to be inserted into one instrument access port of the plurality of instrument access ports;
a plurality of beacons, one beacon of the plurality of beacons is disposed on the camera access port and a respective beacon of the plurality of beacons is disposed on one instrument access port of the plurality of instrument access ports, each beacon of the plurality of beacons is configured to wirelessly communicate with each other and wherein each beacon is coupled to an activation mechanism configured to activate the beacon in response to insertion of an instrument or the endoscopic camera into the corresponding access port; and
a controller configured to determine a position of the endoscopic camera and the plurality of surgical instruments relative to a frame of reference of the endoscopic camera based on the wireless communication between the plurality of beacons during movement of the plurality of beacons.

2. The surgical robotic system according to claim 1, further comprising:
a display configured to show a graphical representation including the position of the endoscopic camera and the plurality of surgical instruments.

3. The surgical robotic system according to claim 2, wherein the graphical representation includes:
a three-dimensional model of a surgical site and models of the endoscopic camera and the plurality of surgical instruments.

4. The surgical robotic system according to claim 3, wherein the display is further configured to show a cone representing a field of view of the endoscopic camera.

5. The surgical robotic system according to claim 2, wherein the graphical representation includes:
a two-dimensional map of a surgical site and symbols representing of the endoscopic camera and the plurality of surgical instruments.

6. The surgical robotic system according to claim 5, wherein the display is further configured to show a circle representing a field of view of the endoscopic camera.

7. The surgical robotic system according to claim 2, wherein the display is further configured to display video feed of a field of view of the endoscopic camera and a representation of at least one of direction or distance of a surgical instrument of the plurality of surgical instruments relative to the endoscopic camera when the surgical instrument is located outside the field of view.

8. A surgical robotic system comprising:
a plurality of robotic arms each holding an access port of a plurality of access ports;
a plurality of surgical devices and an endoscopic camera, each of which is configured to be inserted into one access port of the plurality of access ports;
a plurality of beacons, each of which is disposed on one access port of the plurality of access ports, wherein a respective beacon of the plurality of beacons is configured to wirelessly communicate with each other and is coupled to an activation mechanism configured to activate the beacon in response to insertion of a surgical device of the plurality of surgical devices into the corresponding access port; and
a controller configured to determine a position of each surgical device of the plurality of surgical devices relative to a frame of reference of the endoscopic camera based on the wireless communication between the plurality of beacons during movement of the plurality of beacons.

9. The surgical robotic system according to claim 8, further comprising:
a display configured to show a graphical representation including the position of each surgical device.

10. The surgical robotic system according to claim 9, wherein the graphical representation includes:
a three-dimensional model of a surgical site and models of the plurality of surgical devices.

11. The surgical robotic system according to claim 9, wherein the graphical representation includes:
a two-dimensional map of a surgical site and symbols representing of the plurality of surgical devices.

12. The surgical robotic system according to claim 8, wherein the plurality of surgical devices includes at least one endoscopic camera.

13. The surgical robotic system according to claim 8, wherein the plurality of surgical devices includes a plurality of surgical instruments.

14. The surgical robotic system according to claim 8, wherein each beacon of the plurality of beacons is configured to obtain at least one parameter of the wireless communication.

15. The surgical robotic system according to claim 14, wherein the parameter of the wireless communication includes at least one of time of flight or angle of arrival measurements.

16. The surgical robotic system according to claim 15, wherein the controller is further configured to determine the position of each surgical device of the plurality of surgical devices using at least one trilateration or triangulation based on the parameter of the wireless communication.

17. A method for tracking position of surgical robotic instruments, the method comprising:

activating a plurality of beacons, each of which is disposed on one access port of a plurality of access ports each held by a robotic arm, wherein a respective beacon of the plurality of beacons is configured to wirelessly communicate with each other and wherein each beacon of the plurality of beacons is coupled to an activation mechanism configured to activate the corresponding beacon in response to insertion of a surgical device of a plurality of surgical devices or an endoscopic camera into the corresponding access port;

determining a position of each surgical device of the plurality of surgical devices each of which is inserted into one access port of the plurality of access ports relative to a frame of reference of the endoscopic camera based on the wireless communication between the plurality of beacons during movement of the plurality of beacons; and displaying a graphical representation including the position of each surgical device.

18. The method according to claim 17, wherein displaying further includes displaying at least one of a three-dimensional model of a surgical site and models of the plurality of surgical devices or a two-dimensional map of a surgical site and symbols representing of the plurality of surgical devices.

19. The method according to claim 18, further comprising:

measuring at least one parameter of the wireless communication at each beacon of the plurality of beacons, wherein the parameter of the wireless communication includes at least one of time of flight or angle of arrival measurements.

20. The method according to claim 19, further comprising:

determining the position of each surgical device of the plurality of surgical devices using at least one trilateration or triangulation based on the parameter of the wireless communication.

* * * * *